US006365778B1

(12) United States Patent
Gallas et al.

(10) Patent No.: US 6,365,778 B1
(45) Date of Patent: Apr. 2, 2002

(54) PROCESS FOR THE PREPARATION OF N-ALKYPOLYHYDROXYALKYLAMINES FROM MONOALKYLAMINE AND REDUCING SUGAR

(75) Inventors: Andreas Gallas, Burgkirchen; Johann Franz Hanauer, Unterneukirchen, both of (DE); Hubert Seitz, Reinach/BL (CH); Frank Weinelt, Burgkirchen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/521,480

(22) Filed: Mar. 9, 2000

(51) Int. Cl.$^7$ .......................................... C07C 209/116
(52) U.S. Cl. .................. 564/749; 564/471; 564/472; 564/473; 564/480; 564/507
(58) Field of Search ................................ 564/471, 472, 564/473, 487, 507

(56) References Cited

U.S. PATENT DOCUMENTS 2,016,962 A  11/1935  Flint et al. .................. 536/55.3

5,625,098 A  * 4/1997  Kao et al. .................... 564/487

FOREIGN PATENT DOCUMENTS

| EP | 0 536 939 | 3/1996 |
| WO | WO 92/06073 | 4/1992 |
| WO | WO 92/08687 | 5/1992 |
| WO | WO 93/03004 | 2/1993 |

* cited by examiner

Primary Examiner—Richard L. Raymond
(74) Attorney, Agent, or Firm—Richard P. Silverman

(57) ABSTRACT

Aqueous, alcoholic or aqueous-alcoholic solutions of a monoalkylamine and a reducing sugar are simultaneously injected into a mixing unit and the two solutions are mixed under turbulence in the mixing unit for 6 seconds to 5 minutes at a temperature of 25 to 60° C. and a pressure of 50 to 90 bar. The mixture is then added to a hydrogenation reactor and hydrogenated with hydrogen in the presence of a hydrogenation catalyst. An alkylpolyhydroxyalkylamine is obtained in high yield and with high purity.

13 Claims, No Drawings

PROCESS FOR THE PREPARATION OF N-ALKYPOLYHYDROXYALKYLAMINES FROM MONOALKYLAMINE AND REDUCING SUGAR

BACKGROUND OF THE INVENTION

The invention relates to a process for the preparation of N-alkylpolyhydroxyalkylamines from monoalkylamine and reducing sugar, in which the alkylamine and the reducing sugar are first mixed together in solution, the solution obtained is hydrogenated with hydrogen in the presence of a hydrogenation catalyst and the N-alkylpolyhydroxyalkylamine formed is obtained by removal of the hydrogenation catalyst. Such a process is disclosed, for example, in U.S. Pat. No. 2,016,962, WO-A-92/06073, WO-A-92/08687, WO-A-93/03004 and EP-A-0 536 939, wherein in the three WO publications a detailed description concerning the bringing into contact of monoalkylamine and sugar is given. It is essentially carried out by bringing the sugar and excess alkylamine together at a temperature of approximately 10 to 60° C. and atmospheric pressure. Thus in Example I of WO 93/03004 an aqueous methylamine solution, glucose and ethanol are mixed together at room temperature and the solution obtained is allowed to stand overnight. In Examples IX, XI and XII, an aqueous glucose solution is slowly added to an aqueous methylamine solution at a temperature of 10 to 20° C. and, in turn, atmospheric pressure, whereupon the solution in Example XI is stirred for approximately 30 minutes and in Example XII for approximately 2 hours.

As emerges from the prior art, in particular WO-A 93/03004, the preparation of the solution or mixture from the sugar and the alkylamine, which is then hydrogenated, has an important role with respect to yield of N-alkylpolyhydroxyalkylamine and its content of coloring by-products and other impurities.

SUMMARY OF THE INVENTION

It has surprisingly been found that a high yield of N-alkylpolyhydroxyalkylamine having high color quality and purity is obtained if the solution to be hydrogenated is prepared by mixing the N-alkylamine and the sugar in each case as a solution using pressure and turbulent flow for at most 5 minutes. It is furthermore advantageous if the solution is exposed to the hydrogenation conditions immediately after expiry of the mentioned mixing time.

DESCRIPTION OF THE PREFERRED EMBODIMENTS

The process according to the invention accordingly comprises carrying out the mixing together of monoalkylamine and sugar by injecting the monoalkylamine and the reducing sugar, in each case in the form of an aqueous, alcoholic or aqueous/alcoholic solution, simultaneously into a mixing unit and keeping the solution in the mixing unit under turbulence at a temperature of 25 to 60° C., preferably 40 to 50° C., and a pressure of 50 to 90 bar, preferably 60 to 80 bar, for 3 seconds to 5 minutes, preferably 10 seconds to 1 minute.

The alkylamine is preferably employed as a 10 to 50% strength by weight solution and the sugar as a 40 to 75% strength by weight solution in water, alcohol or in a mixture of water and alcohol, water on its own being preferred as a solvent. The alkylamine solution is preferably fed into the mixing space at a temperature of 10 to 30° C. and the sugar solution at a temperature of 40 to 60° C.

During the mixing of the two solutions, heat is liberated (exothermic reaction). The specified temperature of the solutions which are introduced into the mixing space is adjusted to the temperature to be adhered to in the mixing of 25 to 60° C., preferably 40 to 50° C., taking into account the exothermic reaction, so that the mixing temperature mentioned is guaranteed without further measures (such as cooling or heating). In the case of alcohol as a solvent, the $C_1$–$C_4$-alkanols, such as methanol, ethanol and isopropanol and the low molecular weight glycols such as monoethylene glycol, diethylene glycol and propylene glycol or mixtures of these alcohols and glycols are preferred.

The mixing of the alkylamine solution and the sugar solution is carried out according to the invention in a turbulent flow adhering to the specified temperature and pressure values and the specified time (residence time), during which mixing should be carried out under turbulence. The mixing space or mixing unit used is preferably a tube which withstands the pressure to be adhered to. Turbulence can be achieved, for example, by putting the known turbulence-producing internals in the pressure-resistant tube. Such tubes are, as is known, designated as static mixers. To adhere to the residence time according to the invention of 6 seconds to 5 minutes, preferably 10 seconds to 1 minute, the diameter of the tube is clearly to be adjusted to the amount of solution employed. The alkylamine solution and the sugar solution are simultaneously introduced (preferably separately from one another) into the mixing unit, it clearly being possible to use a somewhat higher pressure in comparison with the pressure in the mixing unit.

The solution resulting after mixing in the mixing space is preferably immediately subjected to hydrogenation. In order to achieve immediately subsequent hydrogenation, it is preferred to inject the solution, after the specified residence time in the mixing space, directly into a stirring autoclave into which the hydrogenation catalyst has already been introduced and in which the hydrogenation temperature and the hydrogen pressure necessary for the hydrogenation have already been adjusted. This hydrogen pressure is 25 to 100 bar, preferably 40 to 80 bar, and the hydrogenation temperature is 40 to 85° C., preferably 50 to 80° C. These hydrogenation conditions are maintained according to the invention until virtually no more hydrogen is absorbed (the hydrogenation time is in general 30 minutes to 5 hours).

According to a preferred embodiment of the process according to the invention, the hydrogenated solution is first thermally formed, stabilized and only then is the N-alkylpolyhydroxyalkylamine removed. The thermal stabilization is preferably itself carried out following the hydrogenation in the stirring autoclave, the hydrogenated solution being heated (at the mentioned temperature of 40 to 100° C., preferably 25 to 85° C., and under a hydrogen pressure of 50 to 80 bar, preferably 40 to 80 bar) to 95 to 100° C., preferably 95 to 105° C. The increase in the temperature to these higher values while retaining the hydrogen present is preferably carried out continuously and slowly, that is in a time of approximately 30 to 150 minutes, preferably 40 to 110 minutes (it goes without saying that with the temperature increase the hydrogen pressure in the autoclave also increases to a greater or lesser extent). As soon as the solution has reached the higher temperature values, it is brought to a temperature of 60 to 90° C., preferably 70 to 80° C., by cooling, which should preferably take place rapidly (15 to 30 minutes). During the stabilization phase, consisting of increasing the temperature and lowering the temperature, virtually no hydrogen is absorbed by the hydrogenated solution, and hydrogen is not significantly added to nor removed from the system, as already mentioned above.

After the hydrogenation and the thermal stabilization which is optionally carried out, the N-alkylpolyhydroxyalkylamine is obtained from the reaction product. This is preferably carried out according to the invention by first exposing the reaction product in the stirring autoclave in which the hydrogenation and, if appropriate, thermal stabilization have been carried out to a sedimentation phase while stopping the stirring. During this phase, a temperature of 60 to 90° C., preferably 70 to 80° C., and a hydrogen pressure of 70 to 95 bar, preferably 80 to 90 bar, is set (if this temperature and this pressure are not already present anyway) and maintained. In the sedimentation phase (which in general lasts 10 to 40 minutes), the hydrogenation catalyst is deposited on the bottom of the stirring autoclave, and an essentially clear solution is obtained, which contains the N-alkylpolyhydroxyalkylamine. The clear solution is decanted off (forced out), preferably with the aid of a dip tube introduced into the solution. During the decanting-off, the same temperature and the same hydrogen pressure as in the sedimentation are essentially maintained. The decanted-off, essentially clear solution can, if appropriate, additionally be filtered. Removal of the solvent by distillation will then be performed if it is wanted to have the N-alkylpolyhydroxyalkylamine in solvent-free form.

In the process according to the invention, the monoalkylamine and the polyol compound are employed in a molar ratio of approximately 1 to 2 to 1, preferably 1 to 1.6 to 1 (the stoichiometric molar ratio is 1 to 1). It was found that it is advantageous if monoalkylamine is also introduced into the hydrogenation autoclave in which the solution mixed under turbulence is injected for hydrogenation. The amount of alkylamine introduced can vary within wide limits and is in general 0.05 to 3 mol, preferably 0.1 to 1 mol of alkylamine per mole of polyol compound. To avoid too large a total excess of alkylamine, it is preferred to divert the whole or at least a relatively large part of the amount of alkylamine to be introduced from the superstoichiometric amount in the mentioned ratio 1 to 2 to 1 (preferably 1 to 1.6 to 1). Of this superstoichiometric amount of alkylamine, approximately 30 to 100% by weight, preferably 50 to 90% by weight, will thus be introduced into the hydrogenation system.

In the process according to the invention, the hydrogenation catalysts employed are preferably nickel catalysts, Raney nickel being particularly preferred. The amount of hydrogenation catalyst can vary within wide limits and is in general 2 to 20% by weight, preferably 5 to 15% by weight, based on the amount of polyol compound employed.

Regarding the starting compounds, monoalkylamine and reducing sugar, the following may additionally be said:

The monoalkylamine is preferably one of the formula $RHN_2$, in which R is a preferably linear and saturated alkyl group having 1 to 18 carbon atoms, preferably having 1 to 4 carbon atoms, or a hydroxyalkyl group, preferably $C_1$–$C_4$-hydroxyalkyl. Examples are methylamine, ethylamine, propylamine, isopropylamine, 2-hydroxyethylamine, 2-hydroxypropylamine and the like. Methylamine or ethylamine is particularly preferred. Suitable monoalkylamines are furthermore also $C_1$–$C_4$-dialkylamino-$C_2$–$C_6$-alkylamines, for example dimethylaminopropylamine or alkoxyalkylamines of the formula RO—$(CH_2)_n$—$NH_2$, in which R is $C_1$–$C_4$-alkyl and n is a number from 2 to 4.

The polyhydroxyalkyl compounds or reducing sugar compounds employed are preferably monosaccharides, preferably pentoses and hexoses, and oligosaccharides, preferably disaccharides and trisaccharides. Examples of monosaccharides are fructose, glucose, galactose, mannose, sorbose and talose as hexoses and arabinose, ribose and xylose as pentoses. Examples of oligosaccharides (polysaccharides) are lactose, maltose, maltotriose and the like. Of the oligosaccharides, the disaccharides are preferred. Particularly preferred polyols are the hexoses, in particular glucose.

The N-alkylpolyhydroxyalkylamines prepared using the process according to the invention thus correspond to the formula R—NH—Z, in which R has the mentioned meaning and Z is a radical of the mentioned polyhydroxyalkyl compounds. Z is accordingly preferably a radical of the formula —$CH_2$—[—CH(OH)]$_n$—$CH_2OH$, in which n is an integer from 3 to 5, preferably 3 or 4 and particularly preferably 4. Preferably N–$C_1$ to $C_3$-glucamines are thus prepared, preferably from fructose, glucose, galactose, mannose, sorbose or talose or from their mixtures and particularly preferably the corresponding glucamines such as N-methylglucamine and N-ethylglucamine.

Using the process according to the invention, a linear N-alkylpolyhydroxy-alkylamine is obtained which is very pure and is colorless in the crystalline state. It is furthermore obtained in a yield of up to 98% by weight. This is a very high yield in view of the high purity and color quality of the product. The alkylpolyhydroxy-alkylamine obtained furthermore has an only very small content of hydrogenation catalyst (nickel). It also exhibits a high thermal stability, that is it essentially retains the colorless appearance even if the product is heated to relatively high temperatures for a relatively long time. Using the process according to the invention, it is furthermore achieved that the activity of the hydrogenation catalyst is largely retained, in that, in this way, the catalyst is available for a number of batches with identical yield and product quality. As soon as the used catalyst no longer has the desired activity, it is possible to restore its original activity by addition of a relatively small amount of fresh catalyst. The process according to the invention thus guarantees a high product yield and product quality and additionally to this an only small loss of hydrogenation catalyst and catalyst activity.

The invention will now be additionally illustrated in greater detail by examples.

EXAMPLE 1

146 mol of monomethylamine (MMA) in water (20.6 kg of MMA solution) were introduced and treated with 7.5 kg of Raney nickel water mixture as a 70% strength slurry. The mixture was pressurized with 80 bar of hydrogen and heated to 50° C. With stirring, a mixture of 290 mol of glucose as a 70% strength aqueous syrup and 290 mol of MMA in water (40.9 kg of MMA solution) were metered into the MMA solution in the hydrogenation reactor via a static mixer. The mean residence time in the mixing unit was 5 seconds. The mixing unit was adjusted to a temperature of 45° C. During the addition, the hydrogen pressure was kept between 70 and 95 bar and the temperature between 48 and 52° C. After addition was complete, the mixture was kept at the mentioned pressure and the mentioned temperature until hydrogen absorption was no longer discernible, which requires approximately 90 min. After conclusion of the hydrogenation, the heating of the reaction mixture to 100° C. was carried out in the course of 60 min. After reaching the temperature, the mixture was cooled to 80° C. in the course of 20 min and the stirrer was switched off. After a sedimentation time of 30 min at 80° C. and approximately 85 bar, the supernatant solution was decanted off from the catalyst and filtered.

After removal of the excess amine and solvent, white crystals were obtained which melt at 130° C. without discoloration.

EXAMPLE 2

146 mol of N,N-dimethylaminopropylamine (DMAPA) (30.9 kg of DMAPA solution) were introduced and treated with 5.6 kg of Raney nickel water mixture as a 70% strength slurry. The mixture was pressurized with 70 bar of hydrogen and heated to 65° C. With stirring, a mixture of 290 mol of glucose as a 70% strength aqueous syrup and 290 mol of DMAPA in water (61.4 kg of DMAPA solution) were metered into the DMAPA solution in the hydrogenation reactor via a static mixer. The mean residence time in the mixing unit was 60 seconds. The mixing unit was adjusted to a temperature of 45° C. During the addition, the hydrogen pressure in the reaction vessel was kept between 50 and 60 bar and the temperature between 58 and 62° C. After addition was complete, the mixture was kept at the mentioned pressure and the mentioned temperature until hydrogen absorption was no longer discernible, which requires approximately 180 min.

After conclusion of the hydrogenation, the heating of the reaction mixture to 105° C. was carried out in the course of 80 min. After reaching the temperature, the mixture was cooled to 70° C. in the course of 35 min and the stirrer was switched off. After a sedimentation time of 20 min at 70° C. and approximately 90 bar, the supernatant solution was decanted off from the catalyst and filtered.

EXAMPLE 3

58 mol of methoxypropylamine (MOPA) in water (25.8 kg of MOPA solution) were introduced and treated with 11.25 kg of Raney nickel water mixture as a 70% strength slurry. The mixture was pressurized with 40 bar of hydrogen and heated to 70° C. With stirring, a mixture of 290 mol of glucose as a 70% strength aqueous syrup and 290 mol of MOPA in water (129 kg of MOPA solution) were metered into the MOPA solution in the hydrogenation reactor via a static mixer. The mean residence time in the mixing unit was 15 seconds. The mixing unit was adjusted to a temperature of 40° C. During the addition, the hydrogen pressure in the reaction vessel was kept between 80 and 90 bar and the temperature between 65 and 68° C. After addition was complete, the mixture was kept at the mentioned pressure and the mentioned temperature until hydrogen absorption was no longer discernible, which requires approximately 120 min.

After conclusion of the hydrogenation, the heating of the reaction mixture to 95° C was carried out in the course of 50 min. After reaching the temperature, the mixture was cooled to 80° C. in the course of 30 min and the stirrer was switched off. After a sedimentation time of 10 min at 80° C. and approximately 85 bar, the supernatant solution was decanted off from the catalyst and filtered.

What is claimed is:

1. A process for the preparation of N-alkylpolyhydroxyalkylamines from monoalkylamine and reducing sugar, in which separate solutions of the alkylamine and the reducing sugar are first mixed together in solution, the solution obtained is hydrogenated with hydrogen in the presence of a hydrogenation catalyst and the N-alkylpolyhydroxyalkylamine formed is obtained by removal of the hydrogenation catalyst, which comprises mixing together by injecting the monoalkylamine and the reducing sugar, in each case in the form of an aqueous, alcoholic or aqueous/alcoholic solution, simultaneously into a mixing unit and keeping the solution in the mixing unit under turbulence at a temperature of 25 to 60° C. and a pressure of 50 to 90 bar for 6 seconds to less than 5 minutes; and immediately hydrogenating the solution in a hydrogenation reactor to produce a hydrogenated solution comprising N-alkylpolyhydroxyalkylamines.

2. The process as claimed in claim 1, wherein the alkylamine is injected into the mixing unit in the form of a 10 to 50% strength by weight solution and the reducing sugar in the form of a 40 to 75% strength by weight solution.

3. The process as claimed in claim 1, wherein the alkylamine is injected into the mixing unit in the form of a 10 to 50% strength by weight aqueous solution having a temperature of 10 to 30° C. and the reducing sugar in the form of a 40 to 75% strength by weight aqueous solution having a temperature of 40 to 60° C.

4. The process as claimed in claim 1, wherein the solution is kept under turbulence in the mixing unit at a temperature of 40 to 50° C. and a pressure of 60 to 80 bar for 6 seconds to 5 minutes.

5. The process as claimed in claim 1, wherein the solution is kept under turbulence in the mixing unit for 10 seconds to 1 minute.

6. The process as claimed in claim 1, wherein the mixing is carried out under turbulence in a pressure-resistant tube as a mixing unit.

7. The process as claimed in claim 1, wherein the hydrogenation reactor comprises a stirring autoclave.

8. The process as claimed in claim 1, wherein the hydrogenation is carried out by injecting the solution into a stirring autoclave in which Raney nickel is present as a hydrogenation catalyst at a temperature of 40 to 85° C. and a hydrogen pressure of 25 to 100 bar, and hydrogenating the injected solution at this temperature and this hydrogen pressure until hydrogen is essentially no longer absorbed.

9. The process as claimed in claim 1, further comprising thermally stabilizing the hydrogenated solution by bringing the hydrogenated solution to 95 to 110° C. while retaining the hydrogen present in a time from 30 to 150 minutes by continuous temperature increase and, after reaching this temperature, cooling to 60 to 90° C.

10. The process as claimed in claim 1, wherein the separation of the hydrogenated and thermally stabilized product, which essentially consists of N-alkylpolyhydroxyalkylamine and hydrogenation catalyst, is carried out by allowing the hydrogenation catalyst to sediment off from the product at a temperature of 60 to 90° C. and a hydrogen pressure of 70 to 95 bar and decanting off the supernatant N-alkylpolyhydroxyalkylamine while retaining this temperature and this hydrogen pressure.

11. The process as claimed in claim 1, wherein the monoalkylamine and the reducing sugar are employed in the molar ratio of 1 to 2:1.

12. The process as claimed in claim 1, wherein
  a) the monoalkylamine in the form of a 10 to 50% strength by weight aqueous, alcoholic or aqueous/alcoholic solution and the reducing sugar in the form of a 40 to 95% strength by weight aqueous, alcoholic or aqueous/alcoholic solution and in the molar ratio of 1 to 1.6 mol of alkylamine per mole of sugar are injected simultaneously into a pressure-resistant tube as a mixing unit and the solution in the tube is kept under turbulence at a temperature of 25 to 60° C. and a pressure of 50 to 90 bar for 6 seconds to 5 minutes,
  b) the solution obtained in step a) is injected, after expiry of the mixing time mentioned, into a stirring autoclave in which 0.1 to 1 mol of monoalkylamine per mole of sugar employed and Raney nickel as a hydrogenation catalyst are present at a temperature of 40 to 85° C. and a hydrogen pressure of 50 to 80 bar, and the injected solution is hydrogenated at this temperature and this hydrogen pressure until hydrogen is essentially no longer absorbed, and the hydrogenated solution is subjected to a thermal stabilization by bringing the solution to 95 to 100° C. while retaining the hydrogen present in a time of 60 to 150 minutes by continuous temperature increase and, after reaching this temperature, cooling to 60 to 90° C., and wherein c) the separation of the hydrogenated and thermally stabilized product, which essentially consists of N-alkylpolyhydroxyalkylamine and hydrogenation catalyst is carried out by allowing the hydrogenation catalyst to sediment off from the product at a temperature of 60 to 90° C. and a hydrogen pressure of 70 to 95 bar and decanting off the supernatant N-alkylpolyhydroxyalkylamine while retaining this temperature and this hydrogen pressure.

13. The process as claimed in claim 12, wherein, in step a), the monoalkylamine in the form of a 10 to 50% strength by weight aqueous solution having a temperature of 10 to 30° C. and the reducing sugar in the form of a 40 to 75% strength by weight aqueous solution having a temperature of 40 to 60° C. and in the molar ratio of 1 to 1.6 mol of alkylamine per mole of sugar are injected simultaneously into the tube and the solution in the tube is kept under turbulence at a temperature of 40 to 50° C. and a pressure of 60 to 80 bar for 10 seconds to 1 minute.

* * * * *